United States Patent [19]

Measamer et al.

[11] Patent Number: 5,501,690
[45] Date of Patent: Mar. 26, 1996

[54] SUTURING DEVICE

[75] Inventors: John P. Measamer, Cincinnati; Robert F. Welch, Maineville; Brett Swensgard, Massillon, all of Ohio

[73] Assignee: Ethicon Endo-Surgery, Cincinnati, Ohio

[21] Appl. No.: 300,295

[22] Filed: Sep. 2, 1994

[51] Int. Cl.⁶ ..................................................... A61B 17/04
[52] U.S. Cl. ......................... 606/146; 606/144; 606/145; 606/147
[58] Field of Search ........................... 606/139, 145, 606/146, 147

[56] References Cited

U.S. PATENT DOCUMENTS

| | | | |
|---|---|---|---|
| 2,370,545 | 2/1945 | Karle | 606/146 |
| 2,439,383 | 4/1948 | Erickson | 606/146 |
| 2,613,564 | 10/1952 | Giaccaglia et al. | 128/326 |
| 2,737,954 | 3/1956 | Knapp | 606/146 |
| 3,067,748 | 12/1962 | Straith | 128/326 |
| 3,344,790 | 10/1967 | Dorner | 606/146 |
| 3,901,244 | 8/1975 | Schweizer | 606/146 |
| 4,164,225 | 8/1979 | Johnson et al. | 606/146 |
| 4,484,580 | 11/1984 | Nomoto et al. | 606/146 |
| 4,935,027 | 6/1990 | Yoon | 606/146 |

FOREIGN PATENT DOCUMENTS

| | | | |
|---|---|---|---|
| 3203628 | 10/1982 | Germany | A61B 17/04 |
| 3136083 | 3/1983 | Germany | A61B 17/04 |

*Primary Examiner*—Gary Jackson
*Attorney, Agent, or Firm*—Paul A. Coletti

[57] ABSTRACT

The invention described herein is a device for tying knots intracorporeally during laparoscopic surgery. It is intended to simplify the process of tying intracorporeal knots to the point that the average laparoscopist can quickly learn to suture laparoscopically with confidence. The unique features of this invention include: a driven shuttle; integral grasper; the system is reloadable; and the system may have a detachable end effector. The system also may have a multi function handle.

18 Claims, 14 Drawing Sheets

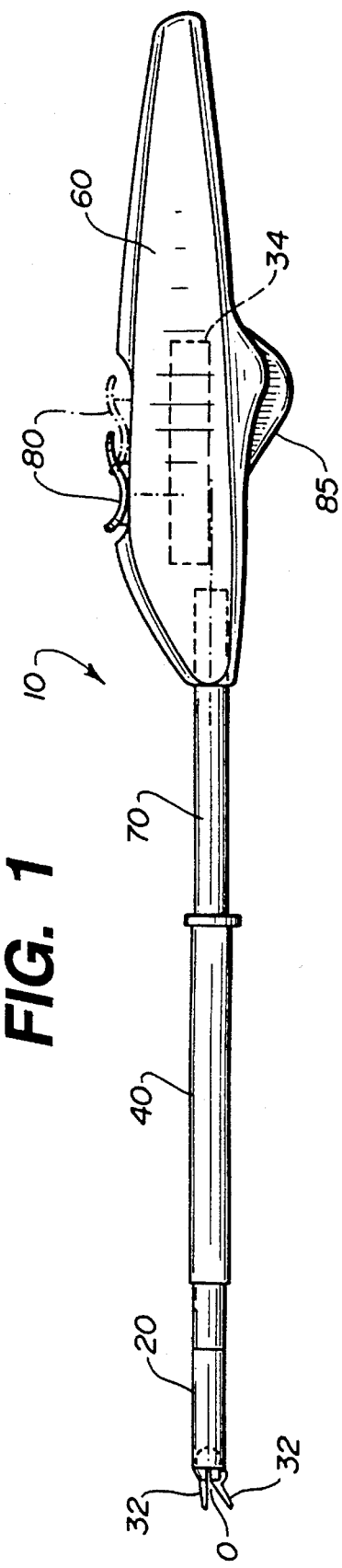
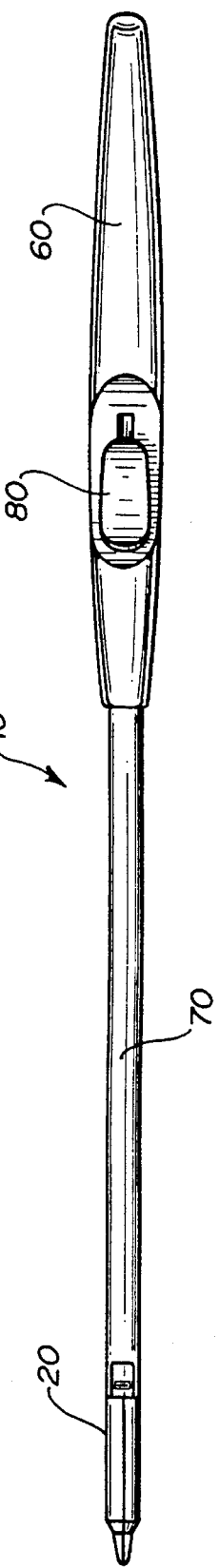
FIG. 1
FIG. 2

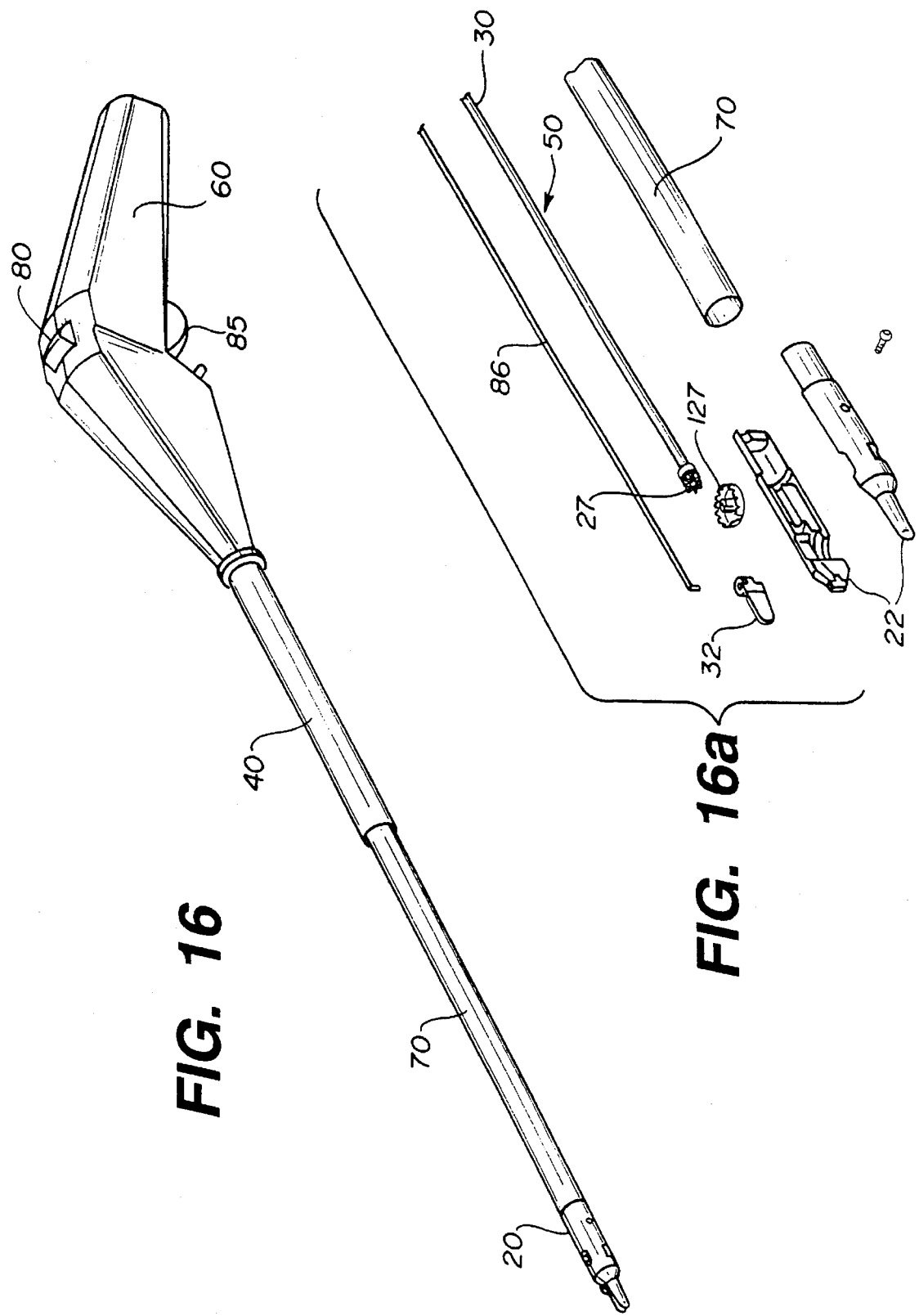

SUTURING DEVICE

BACKGROUND OF THE INVENTION

For surgeons, suturing was long the standard in tissue fastening and repair. But, with the advent of laparoscopic surgery, surgeons were removed from the immediacy of contact with the surgical site that aided suturing. One of the complicating aspects of laparoscopic suturing is tying a knot in the laparoscopic environment. The current techniques are complicated, take many hours to master, and are easily forgotten. As a result, many surgeons avoid laparoscopic suturing, preferring instead to either use alternate tissue fastening methods (clips, staples, endo-loops or loop-sutures), or to avoid those laparoscopic procedures which could require suturing.

SUMMARY OF THE INVENTION

The invention described herein is a device for tying knots intracorporeally during laparoscopic surgery such as those required for urinary stress incontinence (Birch) and gastric anti-reflux procedures (Nissen). It is intended to simplify the process of tying intracorporeal knots to the point that the average laparoscopist can quickly learn to suture laparoscopically with confidence. It is an improvement on the design for a similar system, developed by Dr. Konstantin Zauza, U.S. Ser. No. 143,006 (END 67), incorporated herein by reference.

The unique features of this invention include:

A driven shuttle: The shuttle, the key component in creating the knot, is driven by a mechanism which is activated by the user. This embodiment takes the form of a face gear and pinion, but any mechanism which converts either linear or rotational motion into rotation along a different axis, and causes either one or more overhand throws to be formed in a suture like material, can be used.

Integral grasper: A grasper is included in this invention for the purpose of holding tissue and assist in the positioning of the needle for making a stitch. This grasper is different from the predecessor invention in that the jaws of the grasper, when not in use, serve as the suture lead in to the knot tying mechanism. This minimizes the number of components, and simplifies the use of the grasper.

The system is reloadable: This feature allows the system to be reloaded either with a suture designed to be used specifically with this device, or with a standard suture which has been modified by the user. The modification of the standard suture can be accomplished by the user at the time of use.

The device can be either a single patient disposable unit, or a system with a reusable handle and a detachable end effector designed to be single patient use and disposable. This ensures that the key functional components are new and reliable, and that the system is easy to clean.

DETAILED DESCRIPTION OF THE DRAWINGS

The invention described herein is better understood in conjunction with the following drawings, in which:

FIG. 1 is a side view of the instrument;

FIG. 2 is a top view of the instrument;

FIG. 16 is yet another alternate embodiment; and

FIG. 16a is an exploded view of FIG. 16.

DETAILED DESCRIPTION OF THE INVENTION

The device described herein can be produced in two configurations. One configuration would consist of an applicator 10 and a detachable end effector 20. This configuration would primarily be used when the applicator 10 is reusable. The end effector 20, which would be subject to becoming contaminated and wearing out, would be a single patient use disposable item. The second configuration (FIG. 16), one in which the end effector 10 and applicator 20 are integral, would be used for a single patient use disposable device.

Figure 11:
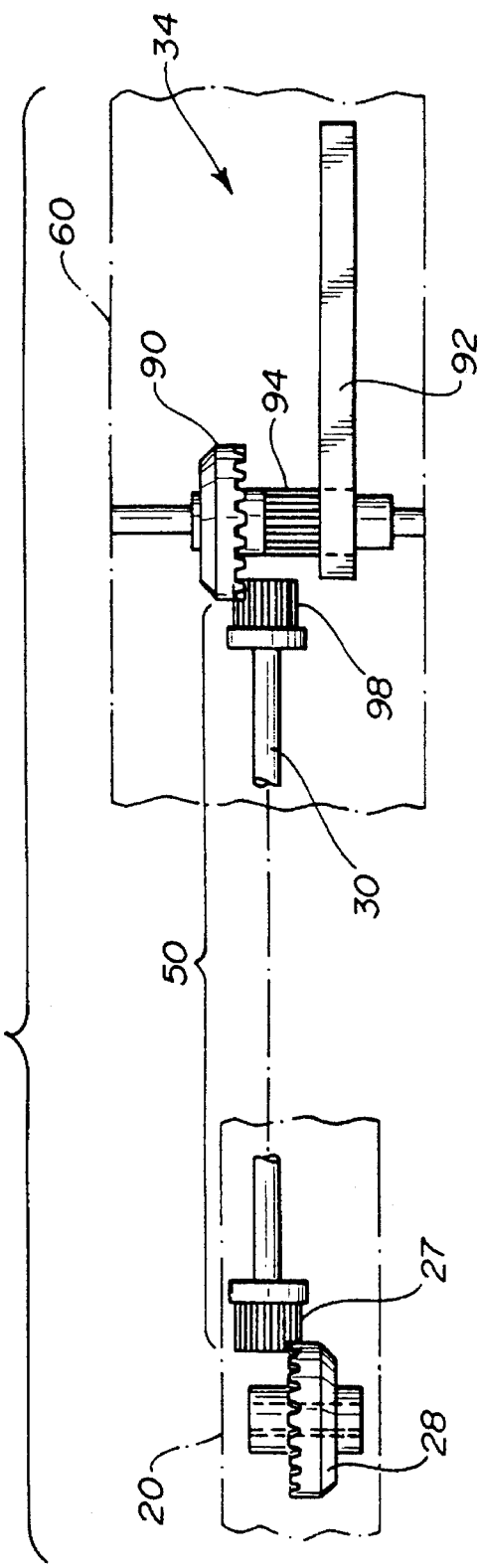
FIG. 11 is an exploded view of the gear mechanism.

When provided as a separate component, the end effector consists of the following sub-systems: 1) A two piece shell or cartridge 22 to hold the mechanisms, and to provide attachment to the applicator 10; 2) The knot tying mechanism 24 forming a drive mechanism consisting of a drive pinion assembly 26 and a shuttle gear 28 forming an alignment means; 3) A grasping system 30 (FIG. 1) consisting of a movable grasper jaw 32 (FIG. 1) and an actuation mechanism 85; and 4) A needle introduction or containment means 40 which will hold the surgical needle in such a position to allow easy introduction into the body cavity and to allow the needle 100 to be easily grasped by a secondary needle driver. These same sub-systems are included in the integral system, except that end effector 20 is permanently attached to the applicator 10 and the drive pinion assembly 26 is replaced by the main drive shaft 50 (FIG. 11).

Figure 10:
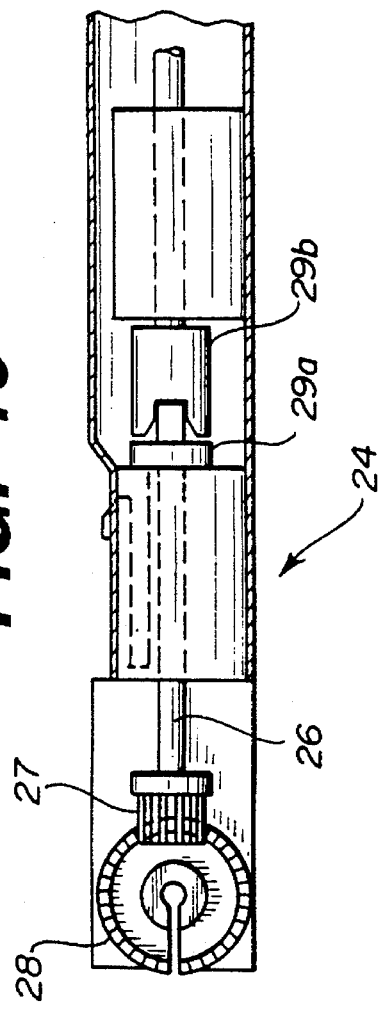
FIG. 10 is a cut away view of an alternate knot tying mechanism.

The drive pinion assembly 26 consists of a pinion gear 27 and a drive shaft 55. The shaft 55 has a coupling means 29a, 29b (FIG. 10) on the proximal end for mating with the applicator 10 in the two piece system. In the single piece system, the drive shaft 30 extends to the applicator handle 60 which contains the actuation mechanism 34.

Figure 14A:
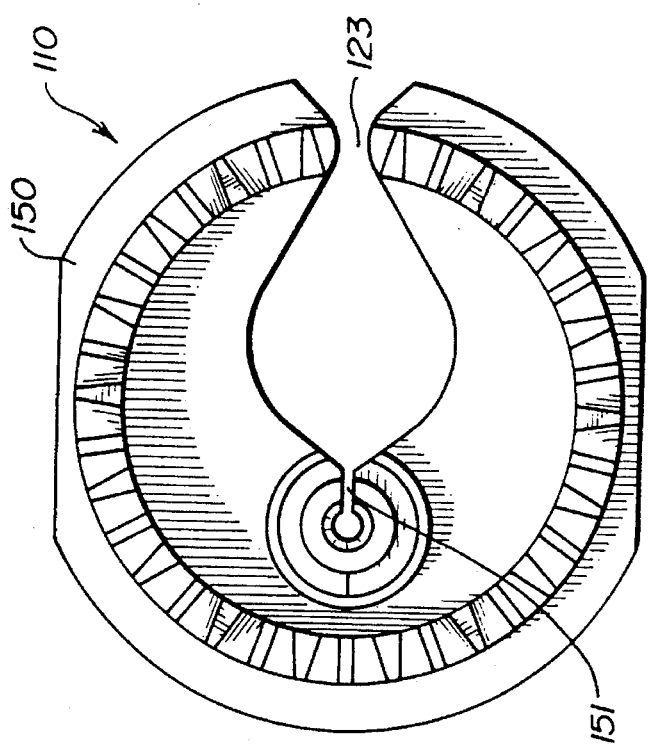
FIG. 14 and 14a are views of the alignment mechanism.
Figure 14:
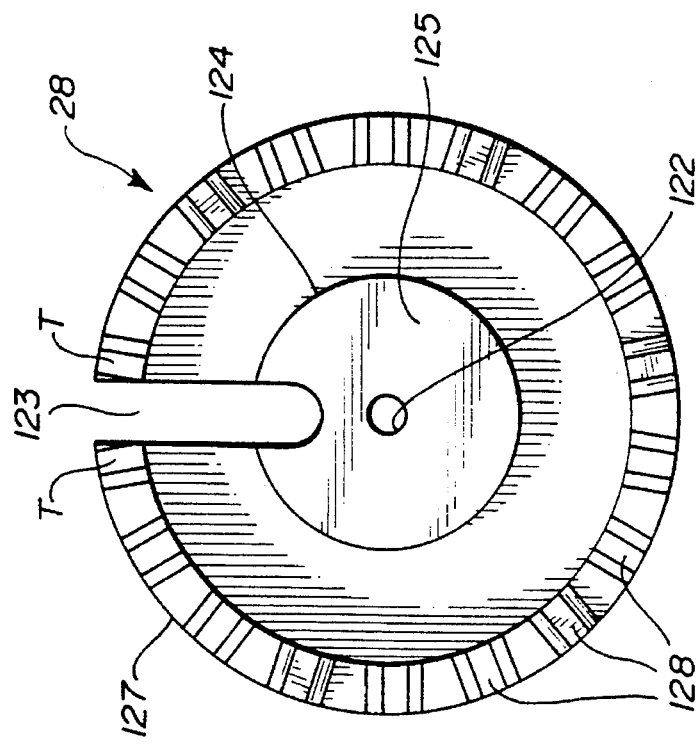

The shuttle gear 28 (FIG. 14) is a modified right angle face gear 127. The teeth 128 of the face gear 127 are designed to mesh with the teeth 126 of the drive pinion 27. The hub region 125 of the face gear 127 consists of a cylinder 124 upon which the face gear 127 is asymmetrically mounted. A radial notch 123 is cut from the shuttle gear 28, passing between two teeth T on the face gear 127 and into the hub 125 of the assembly 28. This notch 123 may be rectangular in cross section, or it may open into a circular opening within the hub section. A hole 122, offset slightly from the centerline, protrudes through the hub 125 of the face gear 127, parallel to the long axis. The hole is located diametrically opposite to the above-described notch 123. The hole could be provided with a counter bore on one or both ends of the hole. The hole is sized to accept a surgical sutures, but is too small to pass a ferrule or knot tied on that suture. A counter bore is sized to accept a knot or ferrule on the end of the suture and is deep enough to allow the knot or ferrule to be completely recessed in the counter bore.

(Another embodiment would to remove the center hub of the face gear. In this embodiment, support and guidance for the shuttle gear 110 (FIG. 14a) will be provided by a ridge or groove 150 located on the circumference of the shuttle gear.)

A shuttle gear assembly is created by attaching the free end of a short length of suture, attached to a surgical needle 100, to the shuttle gear 28. The free end of the suture is passed through the hole in the shuttle gear hub. A knot is tied on the free end of the suture, which in turn is pulled back into the counter bore. This locks the sutures to the shuttle gear 28. A small amount of adhesive may be placed in the counter bore to lock the suture in place. (An alternate method of assembly would be to provide a commutation 151 (FIG. 14a) between the aforementioned radial slot and the suture hole. In this embodiment, the suture assembly (FIG. 15), consisting of a short length of suture 160 with a surgical needle 100 on one end and a small ferrule 161 or knot on the other, is first placed into the radial slot 151 (FIG. 14a), pulled toward the end of that slot through the commutation means, and locked into the suture hole by pulling the knot or bead located on the free end of the suture into the counter bore. This would allow for reloading the instrument during a procedure, and would allow for standard sutures to be modified by the surgical staff to be used with the instrument.)

The cartridge 20 is a cylinder approximately one to one and a half inches long, and approximately ⅜" in diameter. The cartridge 20 is formed from a two-piece shell 22, 22'. The assembly is cavitated to accept the drive pinion 27 and shuttle gear 28. The cartridge 20 holds these parts in alignment, with the teeth of the drive pinion 27 engaged with the teeth on the shuttle gear assembly 28. Both the shuttle gear assembly and drive pinion assembly are allowed to rotate along their respective long axe. The drive pinion gear assembly 26 is positioned parallel to the long axis of the cartridge 20. The shuttle gear 28 is positioned perpendicular to the long axis of the cartridge 20 and is closer to the distal end of the cartridge assembly.

Figure 3:
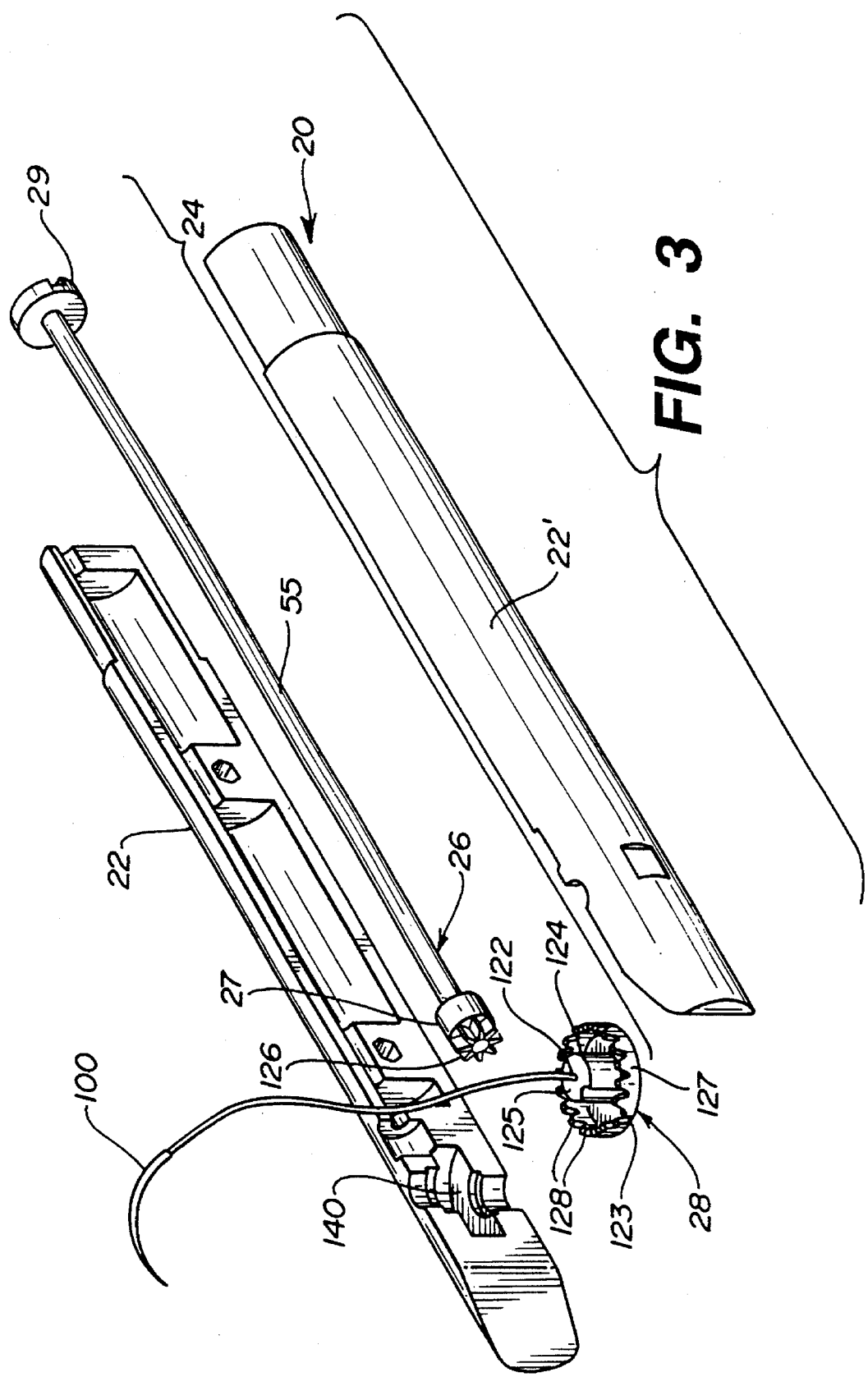
FIG. 3 is an exploded view of the distal end of the instrument.
Figure 4:
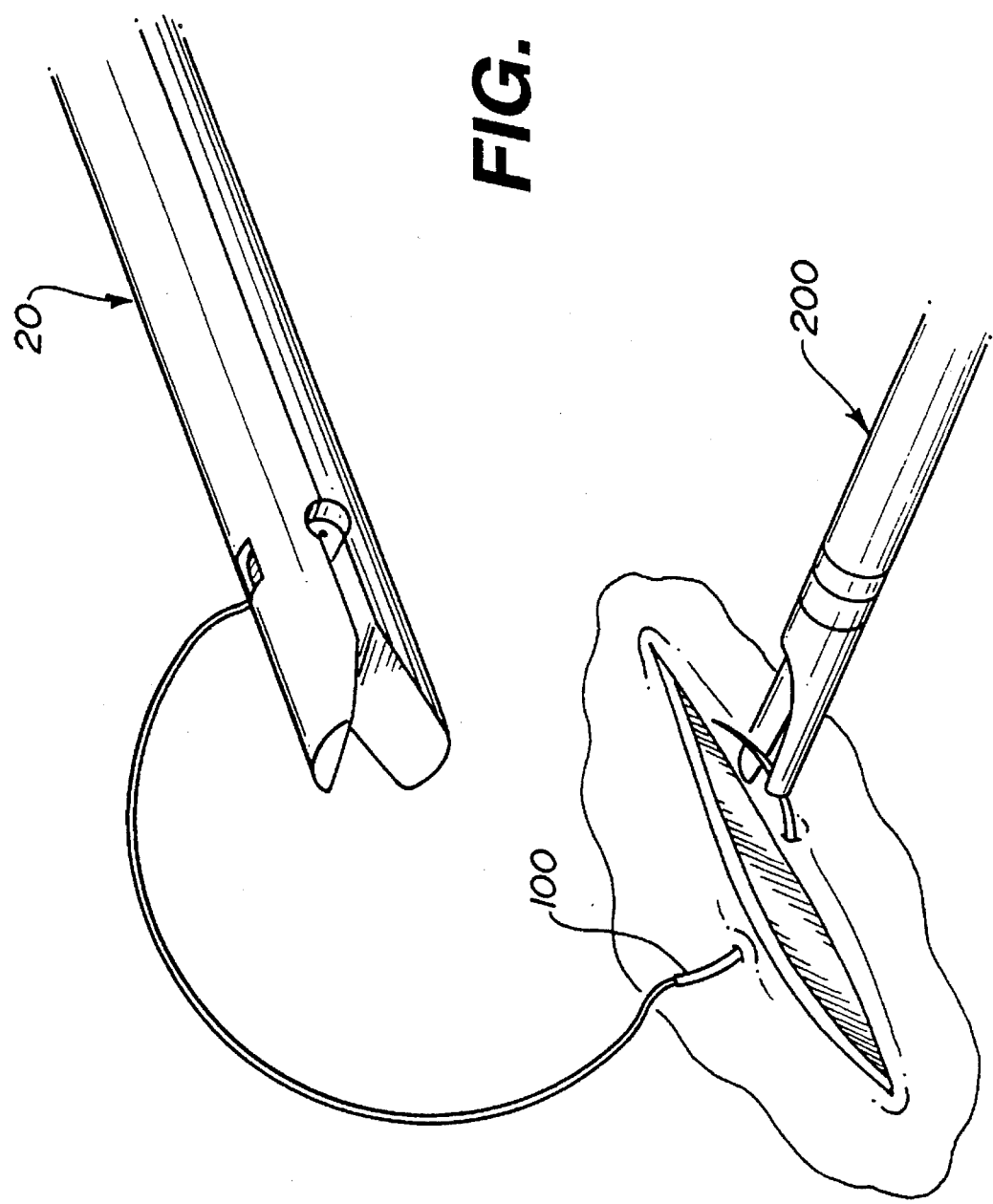
FIGS. 4 through 9 are step sequence views of use of the instrument of this invention.
Figure 5:
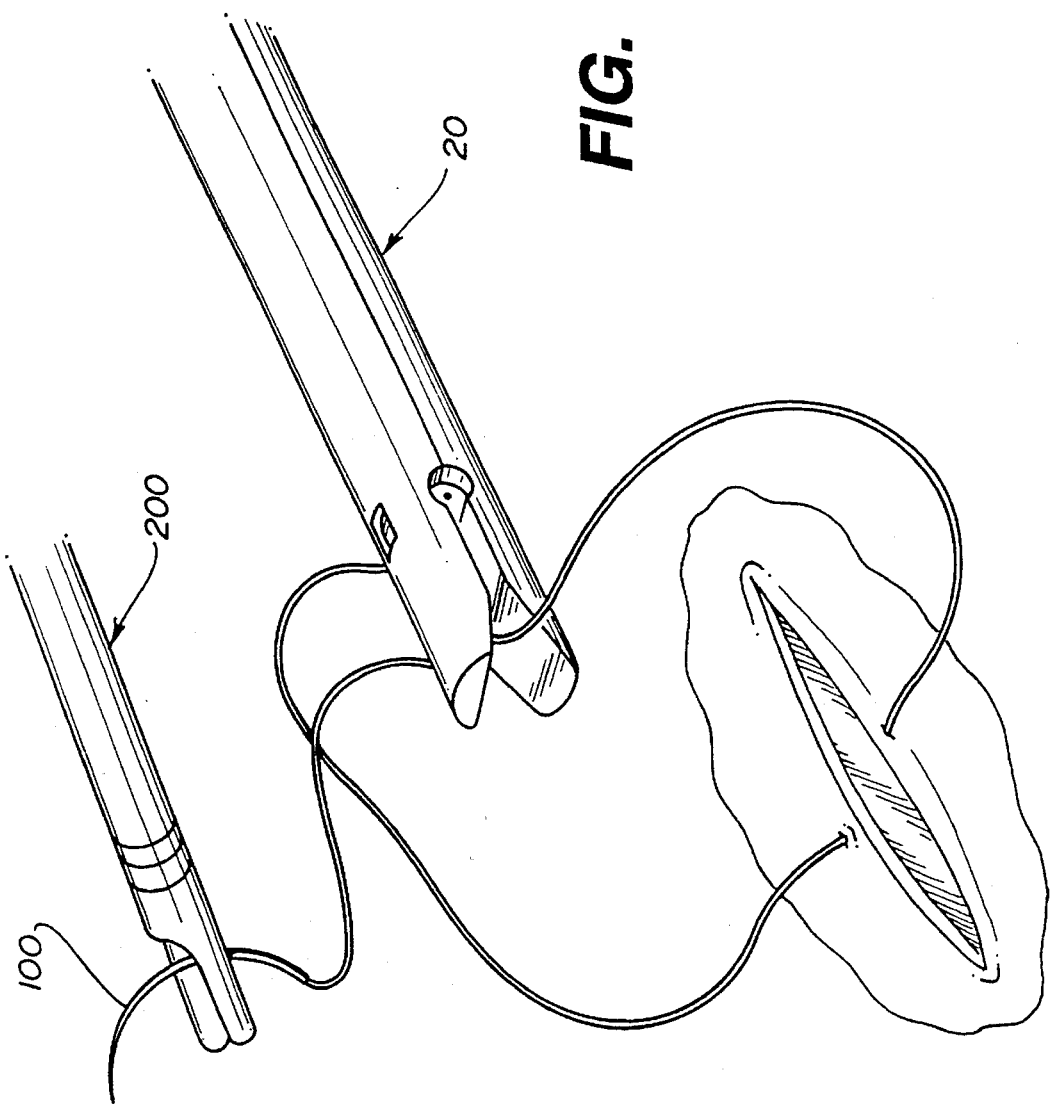
Figure 6:
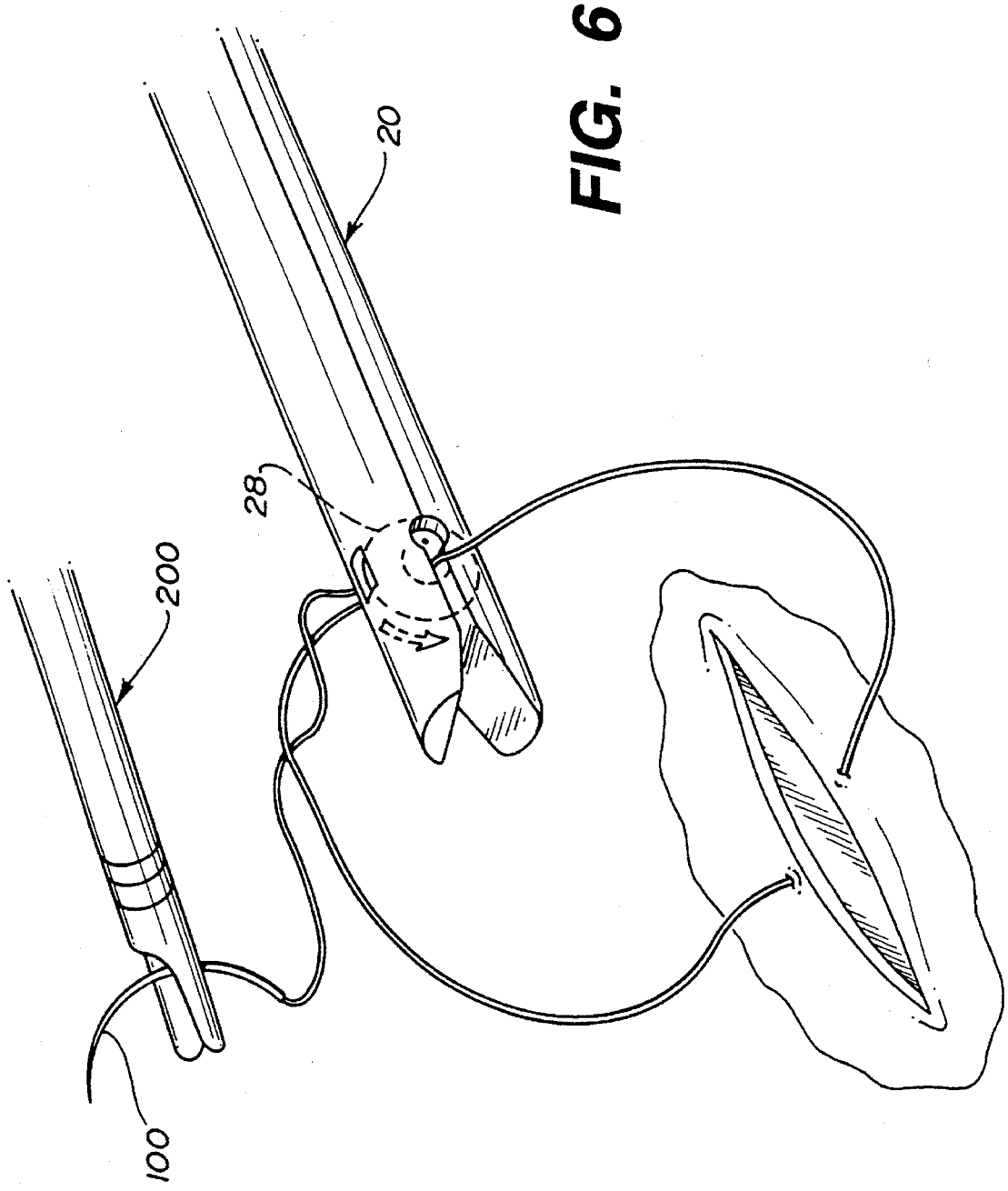
Figure 7:
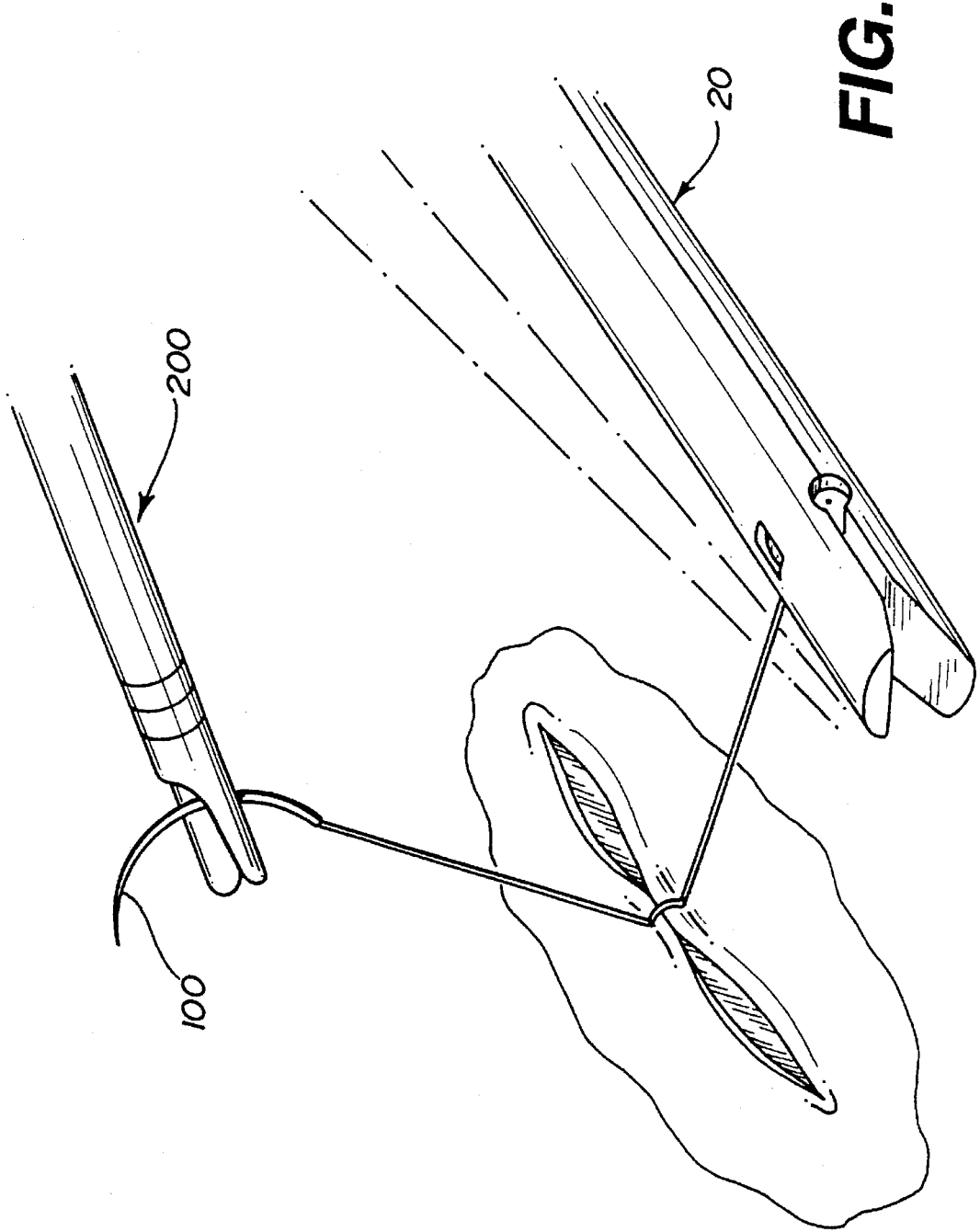
Figure 8:
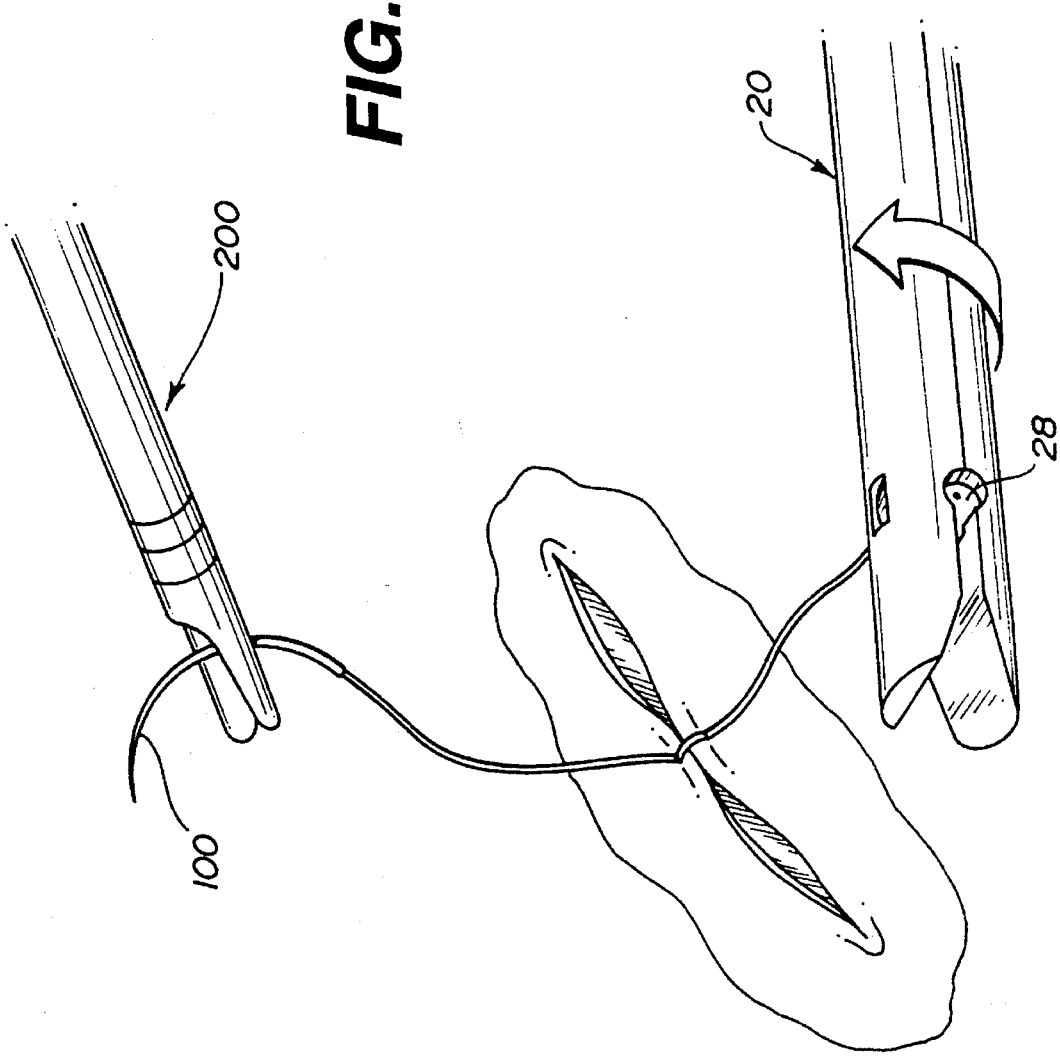
Figure 9:
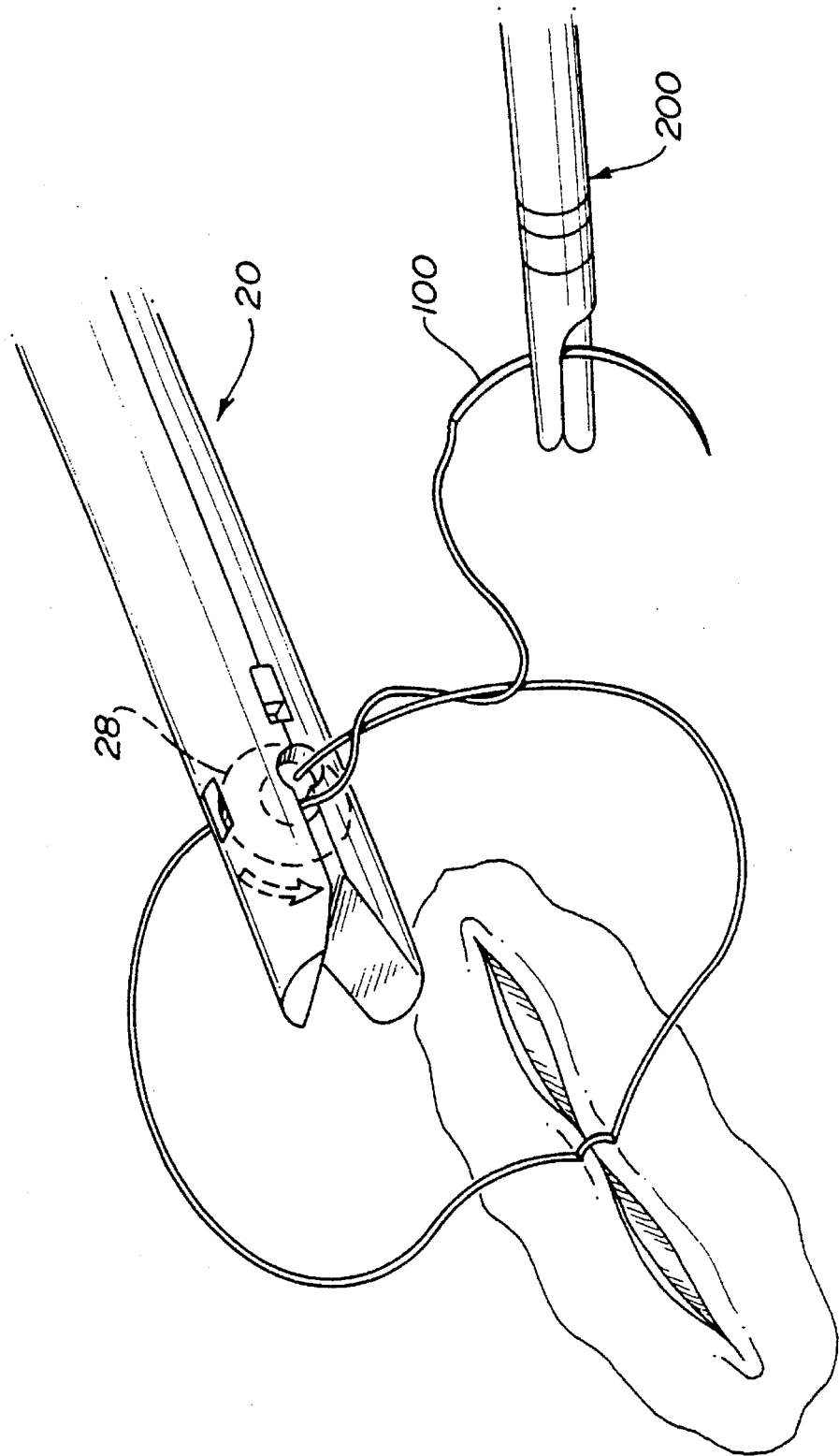

An opening O is provided near the distal end of the cartridge 20 which will allow a length of sutures to be placed into the aforementioned radial notch 123 in the shuttle gear 28. This opening O will be "V" shaped to facilitate the introduction of the sutures. This opening terminates into a series of concentric cylindrical cavitations 140, all positioned perpendicular to the long axis of the cartridge 20 and parallel and co-planar to the parting line plane. These cylinders are sized to accept the shuttle gear 28 and to allow for its free rotation. The innermost cavitation 140 (FIG. 3) extends through the cartridge 20, forming a lip on the outer wall of the cylinder which will retain the shuttle gear 28 along its long axis. The shuttle gear is positioned in the cavitations in the cartridge so that its radial notch 123 extends into the apex of the cartridge "V" slot O describing a lead into the shuttle gear notch.

When the cartridge assembly is complete, the shuttle gear 28 can be rotated by rotating the drive pinion gear assembly 26. The notch 123 in the shuttle gear 28 will line up with the notch O near the distal end of the cartridge 20 once for each revolution of the shuttle gear. The "home" position for the assembly is when the slot O in the cartridge 20 and shuttle gear notch 123 are in alignment.

The applicator 10 consists of a cannula 70, handle assembly 60, an activator for tying knots 80, an activator 85 for the grasper and, internal to the handle 60, the drive mechanism 34 for the drive shaft assembly 50.

Figure 12:
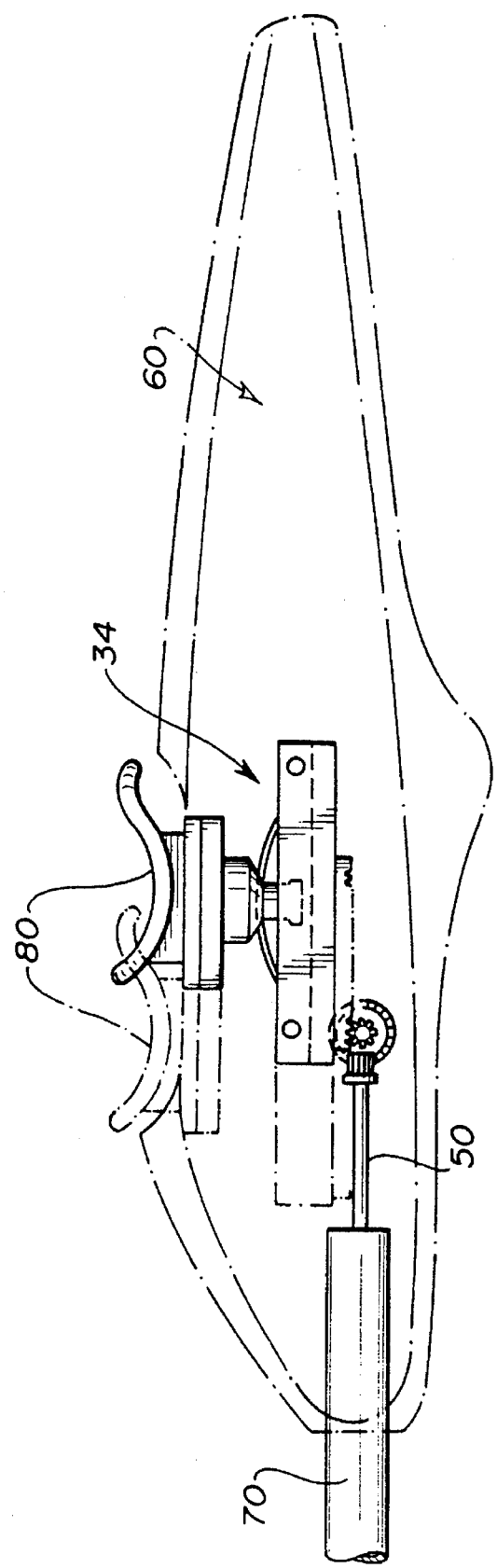
FIG. 12 is a view of the two position handle assembly.
Figure 15:
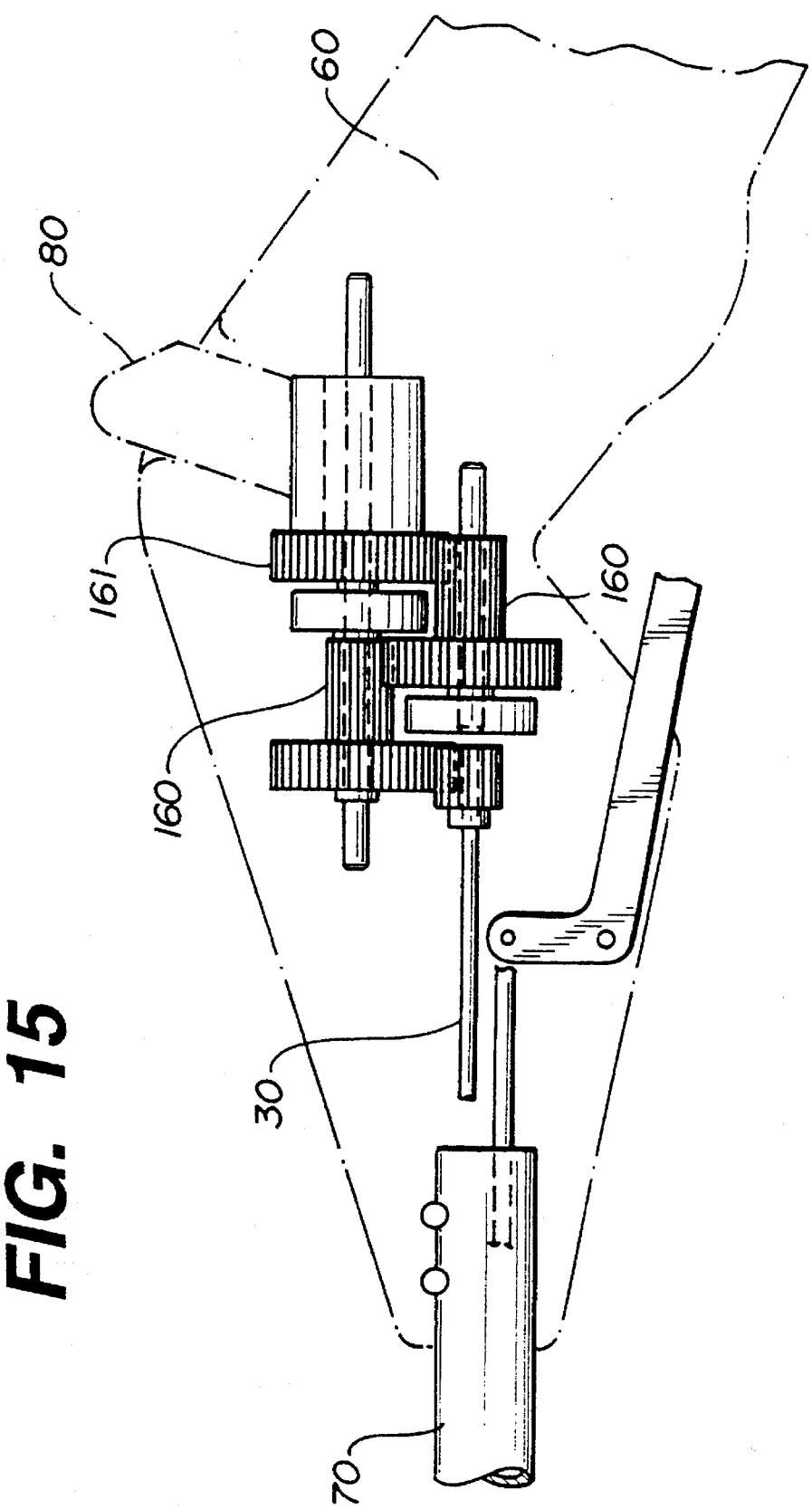
FIG. 15 is an alternate gear mechanism.

The drive mechanism assembly 34 (FIGS. 11 & 12) consists of a sliding rack gear 92 engaged to a first pinion gear 94, a face gear 90 joined to the same shaft as the first pinion gear 94, and another pinion 98 which is attached to the main drive shaft 30, positioned at right angles and engaged with the face gear 99. When the slide rack 92 is moved distally or proximally and parallel to the long axis of the handle 60, the engaged pinion is caused to rotate. This, in turn, causes the face gear 96 to turn which causes the pinion on the main drive shaft 30 to turn. The end result is that the shuttle gear 28 turns a specific number of turns for a given linear motion of the slide rack 92. Motion of the slide rack 92 can be caused by either direct input, from the user, or through a secondary mechanism. An alternate means would be to provide a series of intermeshing stepped spur gears 160 (FIG. 15). Here a small arc-like motion of the input gear 161 would result in multiple revolutions of the drive shaft 30. The drive mechanism could be any mechanism which will convert an input motion from the user into the required motion to activate the driven shuttle.

Figure 13:
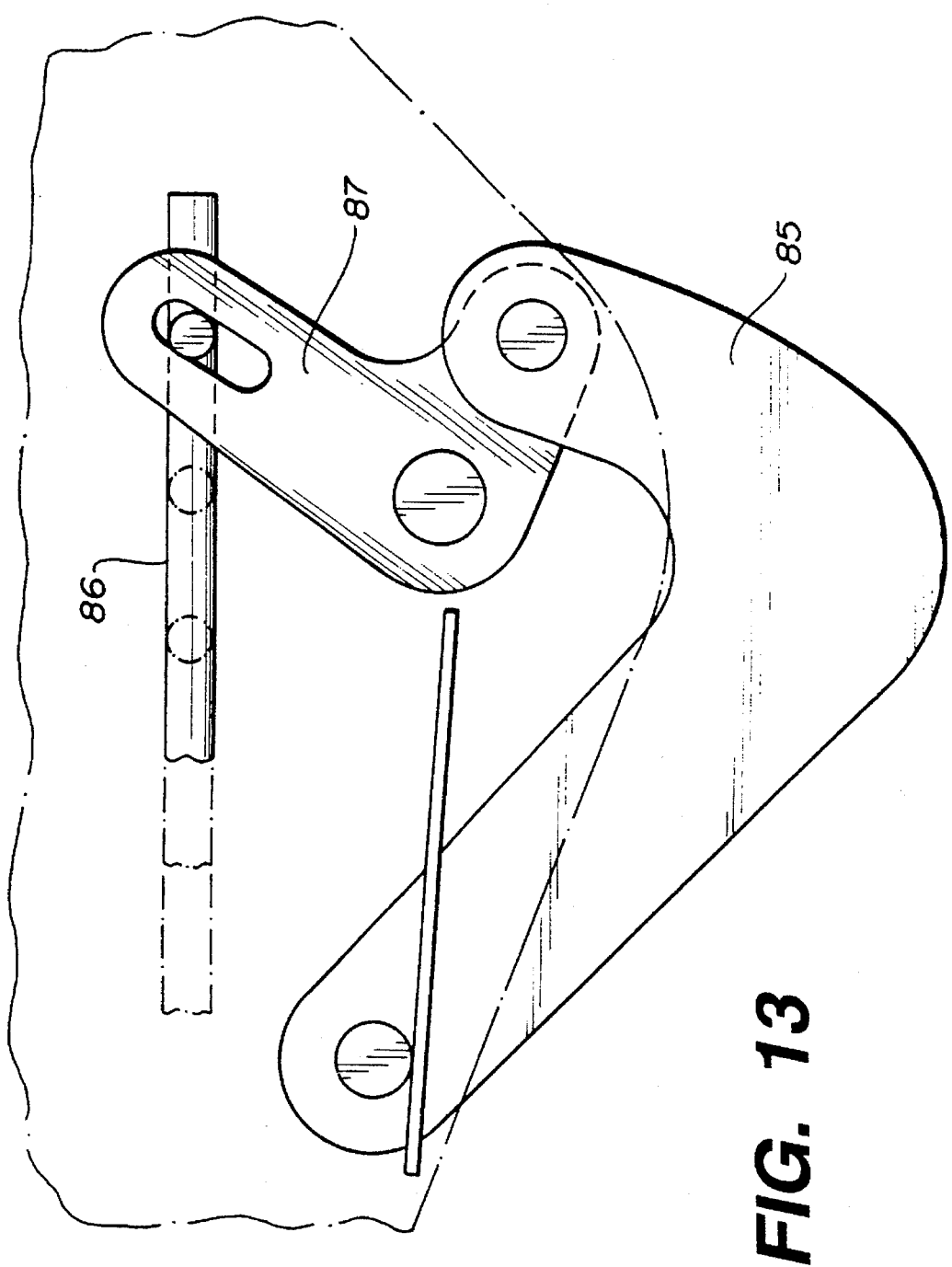
FIG. 13 is a view of the actuation linkage.

The grasper activator 85 (FIG. 13) connects to the grasper jaws 32 (FIG. 1) via a linkage 86, 87 (FIG. 13) that converts an input motion from the user into a linear motion of the grasper link 86. Linear movement of this link causes the grasper jaws 32 to move into approximation.

The applicator cannula 70 provides a means to seal against the trocar used to introduce the device into the body cavity, to provide a support for the drive shaft 30 and the grasper linkage 86, and to provide a coupling means for the cartridge assembly 20 when not an integral part of the instrument. The cannula 70 could also be part of the disposable portion of the configuration wherein the handle is reusable.

As seen in FIGS. 4 through 9, the device functions as follows:

1. If required an end effector is attached to an applicator assembly, a suture is loaded into the shuttle gear, and the needle is covered with the introducer. This assembly is then inserted into the body cavity through a trocar.

2. The needle attached to the suture in the assembly is picked up by a secondary needle holder 200, positioned to make a stitch, and is passed through the tissue.

3. The end effector assembly is positioned so that when the free end of the suture (the one with the needle) is brought into the "V" notch on the distal end of the cartridge, it is on the same side of the cartridge that the suture protrudes from the shuttle. The suture is drawn into this notch until it rests completely within the hub region of shuttle gear.

4. The applicator is then activated, causing the shuttle gear to rotate so that the notch turns into the loop created by the suture. One 360° revolution creates half of a square knot. If a 720° turn is made, half of a surgeon's knot is created.

5. The suture is removed from the cartridge and the ends are pulled apart, drawing the throw of the knot down to the tissue to the desired tightness.

6. The third through the fifth steps are repeated as many times as necessary to secure the knot, alternating direction of shuttle gear rotation for each throw, and tightening the knot between each throw.

7. When the knot is complete, the suture is cut. The needle is removed using the secondary needle holder. The cartridge is withdrawn and the suture is replaced if additional stitches are to be made.

What is claimed is:

1. A surgical suture device comprising:

a shaft;

a rod extending through the shaft and movable therein;

a cartridge connected to said shaft;

a suture fixedly held on a rotatable suture wheel placed on said cartridge said suture wheel having a mechanism for mating with said rod and said cartridge having a proximal end attached to said shaft; and an actuating mechanism connected proximally to said shaft, said actuating mechanism operable to cause said rod to rotate said suture wheel.

2. The device of claim 1 wherein said mechanism mating said rod and said wheel is a set of gears.

3. The device of claim 1 wherein said suture has a needle attached thereto.

4. The device of claim 1 wherein said rod rotates in said shaft.

5. The device of claim 1 further comprising a shaft on either side of the rotatable wheel, parallel to and concentric with the axis of rotation of said rotatable wheel.

6. The device of claim 1 containing a pair of jaws on said cartridge, said jaws pivotable about each other.

7. A surgical suturing device comprising:

a rotatable shuttle having containment means to maintain a plurality of strands of suture like material in opposition;

means to insert said suture like material to said shuttle when said shuttle is maintained by the containment means of the shuttle;

a shaft comprising a drive mechanism connected to said shuttle to transfer motion from the user along said shaft to said shuttle, causing said shuttle to rotate;

alignment means on said shuttle for positioning said shuttle into alignment with said drive mechanism; and a handle connected to said shaft for assembly providing a means to actuate said drive mechanism.

8. The device of claim 7 wherein an actuating input from the user results in at least one overhand throws being created in the suture like material.

9. The device of claim 7 wherein the drive mechanism is a set of intermeshing teeth or gears.

10. The device of claim 7 wherein said rotatable shuttle has a means for fixedly attaching one end of a strand of suture like material.

11. The device in claim 7 wherein said containment means contains an opening in said rotatable shuttle and a narrow slot in the perimeter of the rotatable shuttle.

12. The device in claim 7 wherein said drive mechanism is a rack and pinion gear.

13. The drive mechanism in claim 7 wherein said drive mechanism is a lever attached to a series of stepped spur gears.

14. The device of claim 7 further comprising a coupling means thereby allowing said alignment means or cartridge to separate from said shaft.

15. The device of claim 7 wherein said alignment means contains a mounting and actuating means for at least one movable jaw forming a grasper.

16. The device in claim 7 wherein said handle assembly has a secondary input means which can be used to provide force to said movable jaw.

17. The device of claim 7 containing a shaft wherein said shaft is detachable from said handle.

18. A suture applying mechanism comprising:

a shaft;

a rod extending through the shaft and movable therein;

a cartridge connected to said shaft;

a suture fixedly held on a rotatable suture wheel placed on said cartridge; and an actuating mechanism connected proximally to said shaft, said actuating mechanism operable to cause said rod to rotate said suture wheel in a plurality of directions.

* * * * *